United States Patent
Pudil et al.

(10) Patent No.: US 10,159,957 B2
(45) Date of Patent: Dec. 25, 2018

(54) ZIRCONIUM PHOSPHATE RECHARGING CUSTOMIZATION

(71) Applicant: Medtronic, Inc., Minneapolis, MN (US)

(72) Inventors: Bryant J. Pudil, Plymouth, MN (US); Christopher M. Hobot, Tonka Bay, MN (US)

(73) Assignee: Medtronic, Inc., Minneapolis, MN (US)

( * ) Notice: Subject to any disclaimer, the term of this patent is extended or adjusted under 35 U.S.C. 154(b) by 175 days.

(21) Appl. No.: 15/364,251

(22) Filed: Nov. 29, 2016

(65) Prior Publication Data
US 2017/0087533 A1    Mar. 30, 2017

Related U.S. Application Data

(63) Continuation-in-part of application No. 14/722,068, filed on May 26, 2015, now Pat. No. 9,981,245, and a continuation-in-part of application No. 14/722,119, filed on May 26, 2015, and a continuation-in-part of application No. 14/642,847, filed on Mar. 10, 2015, now Pat. No. 9,974,896, and a continuation-in-part of application No. 14/642,847, filed on Mar. 10, 2015, now Pat. No. 9,974,896, and a continuation-in-part of
(Continued)

(51) Int. Cl.
| | |
|---|---|
| *B01J 20/34* | (2006.01) |
| *B01J 20/02* | (2006.01) |
| *A61M 1/16* | (2006.01) |
| *B01J 39/09* | (2017.01) |

(52) U.S. Cl.
CPC ........ *B01J 20/3475* (2013.01); *A61M 1/1696* (2013.01); *B01J 20/0211* (2013.01); *B01J 20/0292* (2013.01); *B01J 20/3433* (2013.01); *B01J 20/3483* (2013.01); *B01J 39/09* (2017.01)

(58) Field of Classification Search
None
See application file for complete search history.

(56) References Cited

U.S. PATENT DOCUMENTS

| | | |
|---|---|---|
| 3,850,835 A | 11/1974 | Marantz |
| 4,192,748 A | 3/1980 | Hyden |
| | (Continued) | |

FOREIGN PATENT DOCUMENTS

| | | |
|---|---|---|
| CN | 1487853 A | 4/2004 |
| CN | 105658326 A | 6/2016 |
| | (Continued) | |

OTHER PUBLICATIONS

European Search Report for EP App. No. 15812413.1, dated Feb. 2, 2018.
(Continued)

*Primary Examiner* — Richard C Gurtowski
(74) *Attorney, Agent, or Firm* — Kenneth Collier; Roger Hahn

(57) ABSTRACT

The invention relates to devices, systems, and methods for recharging zirconium phosphate in a reusable zirconium phosphate sorbent module. The devices, systems, and methods provide for customization of the zirconium phosphate effluent pH based on the needs of the user and system. The devices systems and methods also provide for calculation of the volumes of recharge solution needed for fully recharging the zirconium phosphate modules.

20 Claims, 3 Drawing Sheets

Related U.S. Application Data application No. 14/261,651, filed on Apr. 25, 2014, now Pat. No. 9,895,477, and a continuation-in-part of application No. 14/261,651, filed on Apr. 25, 2014, now Pat. No. 9,895,477.

(60) Provisional application No. 62/077,159, filed on Nov. 7, 2014, provisional application No. 62/016,613, filed on Jun. 24, 2014, provisional application No. 61/941,672, filed on Feb. 19, 2014, provisional application No. 61/909,372, filed on Nov. 26, 2013.

(56) References Cited

U.S. PATENT DOCUMENTS

| | | | |
|---|---|---|---|
| 4,687,582 | A | 8/1987 | Dixon |
| 6,579,460 | B1 | 6/2003 | Willis |
| 2002/0112609 | A1 | 8/2002 | Wong |
| 2003/0097086 | A1 | 5/2003 | Gura |
| 2005/0056592 | A1 | 3/2005 | Braunger |
| 2006/0241543 | A1 | 10/2006 | Gura |
| 2008/0011664 | A1 | 1/2008 | Karoor |
| 2009/0101552 | A1 | 4/2009 | Fulkerson |
| 2009/0282980 | A1 | 11/2009 | Gura |
| 2010/0004588 | A1 | 1/2010 | Yeh |
| 2010/0078387 | A1 | 4/2010 | Wong |
| 2010/0312172 | A1 | 12/2010 | Hoffman |
| 2011/0017665 | A1 | 1/2011 | Updyke |
| 2011/0048949 | A1 | 3/2011 | Ding et al. |
| 2011/0171713 | A1 | 7/2011 | Bluchel |
| 2011/0272352 | A1 | 11/2011 | Braig |
| 2012/0273354 | A1 | 11/2012 | Orhan et al. |
| 2013/0199998 | A1 | 8/2013 | Kelly |
| 2014/0158588 | A1 | 6/2014 | Pudil |
| 2014/0158623 | A1 | 6/2014 | Pudil |
| 2015/0251161 | A1 | 9/2015 | Pudil |
| 2015/0251162 | A1 | 9/2015 | Pudil |
| 2015/0367055 | A1 | 12/2015 | Pudil |

FOREIGN PATENT DOCUMENTS

| | | |
|---|---|---|
| EP | 2446908 | 5/2012 |
| JP | S5070281 A | 6/1975 |
| JP | S51-55193 | 5/1976 |
| JP | S61164562 | 7/1986 |
| JP | 2981573 | 11/1999 |
| JP | 2005511250 | 4/2005 |
| JP | 200744602 | 2/2007 |
| JP | 200744602 A | 2/2007 |
| JP | 2013502987 | 1/2013 |
| WO | WO 2011/017215 | 2/2011 |
| WO | WO 2013/019994 | 2/2013 |
| WO | WO 2013019179 | 2/2013 |
| WO | 2013101888 | 7/2013 |
| WO | WO 2013/103607 | 7/2013 |
| WO | 2015060914 | 4/2015 |
| WO | 2015199765 | 12/2015 |
| WO | 2015199863 | 12/2015 |
| WO | 2015199864 | 12/2015 |

OTHER PUBLICATIONS

European Search Report for App. No. 15812081.6, dated Mar. 8, 2018.
European Search Report for EP App. No. 15811326.6, dated Feb. 14, 2018.
PCT/US2015/019901 International Search Report and Written Opinion dated Jun. 5, 2015.
PCT/US2015/032492 International Search Report dated Nov. 19, 2015.
PCT/US2015/032492 Written Opinion dated Nov. 19, 2015.
Wheaton, et al., Dowex Ion Exchange Resins—Fundamentals of Ion Exchange; Jun. 2000, pp. 1-9. http://www.dow.com/scripts/litorder.asp?filepath=liquidseps/pdfs/noreg/177-01837.pdf.
PCT/US2016/030304 Written Opinion dated Jul. 27, 2016.
PCT/US2016/030312 Written Opinion dated Jul. 27, 2016.
PCT/US2016/030319 Written Opinion dated Jul. 27, 2016.
PCT/US2016/030320 Written Opinion dated Jul. 27, 2016.
Office Action in App. No. AU 2015280604 dated Apr. 8, 2016.
Wester et al., A regenerable postassium and phosphate sorbent system to enhance dialysis efficacy and device portability: an in vitro study Nephrol Dial Transplant (2013) 28: 2364-2371 Jul. 3, 2013.
John Wm Agar: "Review: Understanding sorbent dialysis systems," Nephrology, vol. 15, No. 4, Jun. 1, 2010, pp. 406-411.
Office Action in App. No. JP 2016-515476 dated Dec. 26, 2016.
PCT/US2015/032494 Written Opinion dated Nov. 19, 2015.
PCT/US2015/032494 International Search Report dated Nov. 19, 2015.
PCT/US2015/019901 International Preliminary Report on Patentability dated May 27, 2016.
PCT/US2015/019901 Written Opinion dated May 27, 2016.
PCT/US2015/019901 Written Opinion dated Jun. 5, 2015.
PCT/US2015/019901 International Search Report dated Jun. 5, 2015.
PCT/US2015/032485 International Preliminary Report on Patentability dated May 11, 2016.
PCT/US2016/030304 International Search Report dated Jul. 27, 2016.
PCT/US2016/030312 Written Opinion dated Jul. 28, 2016.
PCT/US2016/030312 International Search Report dated Jul. 28, 2016.
PCT/US2016/030319 International Search Report dated Jul. 27, 2016.
PCT/US2016/030320 International Search Report dated Jul. 28, 2016.
PCT/US2016/030320 Written Opinion dated Jul. 28, 2016.
PCT/US2015/032485 Written Opinion dated Oct. 16, 2016.
PCT/US2015/032485 International Search Report and Written Opinion dated Oct. 16, 2015.
PCT/US2016/030320 International Preliminary Report on Patentability, dated Apr. 20, 2017.
PCT/US2015/032494 International Preliminary Report on Patentablity dated Dec. 27, 2016.
European Search Report and Supplemental Search Report in European Application No. 14865374.4 dated Jun. 12, 2017.
Japanese Application No. 2016-553344, dated Apr. 24, 2018.

US 10,159,957 B2

ZIRCONIUM PHOSPHATE RECHARGING CUSTOMIZATION

FIELD OF THE INVENTION

The invention relates to devices, systems, and methods for recharging zirconium phosphate in a reusable zirconium phosphate sorbent module. The devices, systems, and methods provide for customization of the zirconium phosphate effluent pH based on the needs of the user and system. The devices systems and methods also provide for calculation of the volumes of recharge solution needed for fully recharging the zirconium phosphate modules.

BACKGROUND

Zirconium phosphate is used in sorbent dialysis to remove waste and unwanted solutes including ammonium, potassium, calcium, and magnesium ions from dialysate. The zirconium phosphate is generally packaged in a sorbent cartridge. Usually, sorbent cartridges are discarded and replaced after use. The discarded sorbent cartridges are broken down and the zirconium phosphate separated from the other sorbent materials. Because zirconium phosphate is expensive and rechargeable, sorbent re-processors treat the recovered zirconium phosphate with chemical solutions. The recycling process requires transporting the materials to reprocessing facilities and involves laborious recycling steps in addition to recharging the sorbent materials. Further, the sorbent material cannot be immediately reused, and must be added to a new sorbent cartridge and repackaged for sale. Conventional methods drive up costs and infrastructure requirements, and increase complexity and waste.

Different patients may require differing dialysate bicarbonate levels for effective treatment. For example, alkalotic patients require a dialysate bicarbonate level lower than other patients. The bicarbonate level of the dialysate is generally controlled by the addition sodium bicarbonate, which acts as a buffer. Bicarbonate ions in the dialysate are in equilibrium with carbon dioxide. The zirconium phosphate effluent pH is the main driver in determining the bicarbonate/carbon dioxide ratio. A lower zirconium phosphate effluent pH will produce more $pCO_2$ which can result in dialysate entering the dialyzer at too low a pH, potentially causing hemolysis. High $pCO_2$ can also cause bubbles to form in the dialysate which can potentially be transferred to the patient. The excess $CO_2$ can be removed by a degasser, such as a membrane contactor degasser, a vacuum degasser, or any other device capable of removing $CO_2$ from solution. A higher zirconium phosphate effluent pH will result in higher bicarbonate concentration, requiring less bicarbonate addition to the dialysate, but may not be usable in treatment of all patients.

Known recharging systems do not control the volume of chemical solutions used in recharging the zirconium phosphate, and instead simply treat the zirconium phosphate with enough recharging chemicals to ensure complete recharging. Recharging zirconium phosphate in this fashion results in the use of higher volumes of recharging chemicals than may be necessary.

Hence, there is a need for systems and methods that can recharge zirconium phosphate in a zirconium phosphate sorbent module. There is also a need for systems and method that can customize the dialysate bicarbonate levels by controlling the zirconium phosphate effluent pH. There is further a need for systems and methods that can control the zirconium phosphate recharging process to create a zirconium phosphate module having a desired effluent pH. The need extends to systems and methods for determining a desired zirconium phosphate effluent pH based on the needs of the patient and system. There is also a need for systems and methods that can calculate the amount of recharging solutions necessary for recharging the zirconium phosphate.

SUMMARY OF THE INVENTION

The first aspect of the invention relates to a method. In any embodiment, the method can include determining a desired initial therapy zirconium phosphate effluent pH based on one or more patient parameters; and recharging zirconium phosphate in a zirconium phosphate sorbent module by pumping one or more recharge solutions through the zirconium phosphate module; the one or more recharge solutions including an acid solution, a base solution, a buffer solution, a salt solution, water, or combinations thereof; wherein the one or more recharge solutions have an acid concentration, a base concentration, a buffer concentration, and a salt concentration to result in the desired initial therapy zirconium phosphate effluent pH.

In any embodiment, the step of pumping the one or more recharge solutions through the zirconium phosphate module can include pumping multiple recharge solutions through the zirconium phosphate module in a sequential order.

In any embodiment, the sequential order can include a first recharge solution containing an acid or buffer, and a second recharge solution containing a sodium salt; or a first recharge solution containing a sodium salt and a second recharge solution containing an acid or buffer.

In any embodiment, the buffer can contain acetic acid and sodium acetate.

In any embodiment, the desired initial therapy zirconium phosphate pH can be between 4.0 and 6.9.

In any embodiment, a single recharge solution can be pumped through the zirconium phosphate module.

In any embodiment, the single recharge solution can be a solution of acetic acid, sodium acetate, and sodium chloride.

In any embodiment, the single recharge solution can have a pH of between 4.2 and 5.0.

In any embodiment, the method can include the step of determining an amount of cations removed by the zirconium phosphate module in a dialysis session prior to the step of pumping the one or more recharge solutions through the zirconium phosphate module.

In any embodiment, a volume of recharge solution used can be based, at least in part, on the amount of cations removed by the zirconium phosphate module.

In any embodiment, the one or more recharge solutions can contain sodium ions in an amount of between 5 and 15 times greater than the amount of cations removed by the zirconium phosphate module.

In any embodiment, the method can include the step of heating the one or more recharge solutions to a specified temperature prior to pumping the one or more recharge solutions through the zirconium phosphate module.

In any embodiment, the acid concentration, base concentration, buffer concentration, and salt concentration can be set based at least in part on the specified temperature.

The features disclosed as being part of the first aspect of the invention can be in the first aspect of the invention, either alone or in combination, or follow a preferred arrangement of one or more of the described elements.

The second aspect of the invention is drawn to a recharger. In any embodiment, the recharger can include a receiving compartment having a zirconium phosphate module inlet and a zirconium phosphate module outlet for receiving a zirconium phosphate module; one or more recharge solution sources, wherein the one or more recharge solution sources are selected from an acid source, a base source, a salt source, a water source, and combinations thereof; a recharging flow path fluidly connected to the one or more recharge solution sources and the zirconium phosphate module inlet, and including at least one pump; a control system determining a desired initial therapy zirconium phosphate effluent pH, and determining a concentration of an acid, a base, a buffer, a salt, or combinations thereof to result in the desired initial therapy zirconium phosphate effluent pH; and the control system controlling an amount of each recharge solution pumped through the recharging flow path.

In any embodiment, the recharger can include one or more valves fluidly connected to the one or more recharge solution sources and the recharging flow path.

In any embodiment, the recharger can include a heater and temperature sensor in the recharging flow path.

In any embodiment, the control system can determine a volume of acid, base, buffer, and salt for recharging the zirconium phosphate module based at least in part on a temperature of one or more recharge solutions.

In any embodiment, the control system can determine a volume of acid, base, buffer, and salt for recharging the zirconium phosphate module based at least in part on an amount of cations removed by the zirconium phosphate module during a dialysis session.

In any embodiment, the one or more recharge solution sources can include at least two recharge solution sources.

In any embodiment, the system can include a static mixer in the recharging flow path for mixing of the acid, base, buffer, or salt.

The features disclosed as being part of the second aspect of the invention can be in the second aspect of the invention, either alone or in combination, or follow a preferred arrangement of one or more of the described elements.

DETAILED DESCRIPTION OF THE INVENTION

Figure 1:
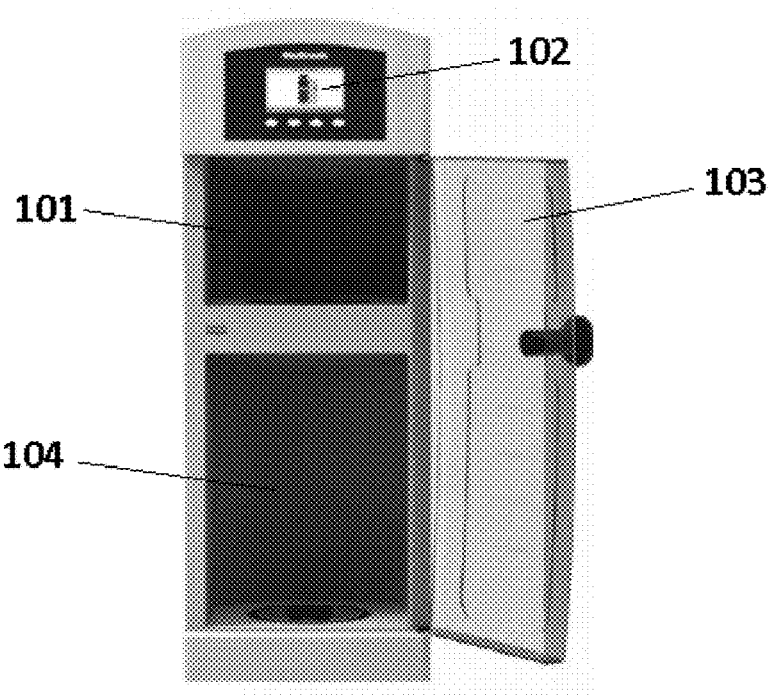
FIG. 1 shows a recharger for recharging a zirconium phosphate module.

Unless defined otherwise, all technical and scientific terms used have the same meaning as commonly understood by one of ordinary skill in the art.

The articles "a" and "an" are used to refer to one or to over one (i.e., to at least one) of the grammatical object of the article. For example, "an element" means one element or over one element.

The term "acid concentration" refers to the number of moles of an acid dissolved in a given volume of water.

The term "acid solution" refers to an aqueous solution having a pH less than 7.

An "acid source" is a fluid or concentrate source from which an acid solution can be obtained.

The term "amount of cations removed by the zirconium phosphate module in a dialysis session" refers to the total number of moles of potassium, calcium, magnesium, ammonium, and other cations adsorbed by zirconium phosphate in the zirconium phosphate module during dialysis therapy.

The term "base concentration" refers to the number of moles of a base dissolved in a given volume of water.

The term "base solution" refers to an aqueous solution having a pH of greater than 7.

A "base source" is a fluid or concentrate source from which a base solution can be obtained.

The term "buffer solution" refers to an aqueous solution containing a weak acid and the conjugate base of the weak acid.

The term "comprising" includes, but is not limited to, whatever follows the word "comprising." Use of the term indicates the listed elements are required or mandatory but that other elements are optional and may be present.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The terms "control," "controlling," or "controls" refers to the ability of one component to direct the actions of a second component.

A "control system" can be a combination of components that act together to maintain a system to a desired set of performance specifications. The control system can use processors, memory and computer components configured to interoperate to maintain the desired performance specifications. The control system can also include fluid or gas control components, and solute control components as known within the art to maintain the performance specifications.

The term "desired initial therapy zirconium phosphate effluent pH" refers to an initial zirconium phosphate effluent pH during therapy set or determined, at least in part, on the needs and capabilities of the system and patient.

The terms "determining" and "determine" refer to ascertaining a particular state or desired state of a system or variable(s).

A "dialysis session" is time period that a patient is treated by dialysis, hemodialysis, hemofiltration, ultrafiltration, or other blood fluid removal therapy.

The term "fluidly connectable," "fluidly connected," and "for fluid connection" refer to the ability of providing for the passage of fluid or gas from one point to another point. The two points can be within or between any one or more of compartments, modules, systems, components, and rechargers, all of any type. The connection can optionally be disconnected and then reconnected.

A "heater" is a component capable of raising the temperature of a substance, container, or fluid.

The term "heating" or to "heat" refers to raising the temperature of a material.

The term "initial therapy zirconium phosphate effluent pH" refers to the pH of a fluid exiting a zirconium phosphate sorbent module at or near the beginning of therapy.

The term "mixing" or to "mix" generally refers to causing or more fluids from any source to combine together. For example, "mixing" can include laminar or turbulent flow at a location in a fluid line or a junction. Another example of "mixing" can include receiving one or more fluids in a component configured to receive fluids from one or multiple sources and to mix the fluids together in the component. Additionally, mixing can refer to the dissolution of a solid or solids with a fluid, wherein the solid or solids is dissolved in the fluid.

A "patient parameter" is any data that gives relevant information about the health status and therapy requirements of a patient.

The term "pump" refers to any device that causes the movement of fluids or gases by applying suction or pressure.

The terms "pumping," "pumped," or to "pump" refers to moving a fluid with a pump.

A "receiving compartment" is a space within a recharger into which a sorbent module to be recharged is placed.

A "recharge solution" is a solution containing appropriate ions for recharging a specific sorbent material. A recharge solution can be a single solution containing all necessary ions for recharging a sorbent material. Alternatively, the recharge solution can contain some of the ions for recharging the sorbent material, and one or more other recharge solutions can be used to recharge the sorbent material.

A "recharge solution source" is any fluid or concentrate source from which a recharge solution can be obtained.

"Recharging" refers to treating a sorbent material to restore the functional capacity of the sorbent material so as to put the sorbent material back into a condition for reuse or use in a new dialysis session. In some instances, the total mass, weight and/or amount of "rechargeable" sorbent materials remain the same. In some instances, the total mass, weight and/or amount of "rechargeable" sorbent materials change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged."

A "recharging flow path" is a path through which fluid can travel while recharging sorbent material in a reusable sorbent module.

To "result in the desired initial therapy zirconium phosphate effluent pH" refers to a recharge solution or solutions that, when used in recharging a zirconium phosphate module, will cause fluid exiting the zirconium phosphate module to have the desired pH at or near the start of therapy.

The term "salt concentration," as used herein, refers to the number of moles of a sodium salt dissolved in a given volume of water.

A "salt solution" refers to an aqueous solution containing dissolved sodium and counter ions.

A "salt source" is a fluid or concentrate source from which a salt solution can be obtained.

The term "sequential order" refers to two or more events occurring at different times, as opposed to simultaneously.

The terms "set based at least in part on" or "set based on" refer to a calculation of a parameter value, wherein the value is a function of at least one other variable.

A "sorbent cartridge module" or "sorbent module" means a discreet component of a sorbent cartridge. Multiple sorbent cartridge modules can be fitted together to form a sorbent cartridge of two, three, or more sorbent cartridge modules. In some embodiments, a single sorbent cartridge module can contain all of the necessary materials for dialysis. In such cases, the sorbent cartridge module can be a "sorbent cartridge."

The term "specified temperature" is a temperature range calculated or determined prior to recharging a zirconium phosphate module.

A "static mixer" is a component configured to receive fluids from one or multiple sources and to mix the fluids together. The static mixer may include components that agitate the fluids to further mixing.

The term "temperature sensor" refers to a device for measuring the temperature of a gas or liquid in a vessel, container, or fluid line.

A "valve" is a device capable of directing the flow of fluid or gas by opening, closing or obstructing one or more pathways to control whether or not the fluid or gas to travel in a particular path. One or more valves that accomplish a desired flow can be configured into a "valve assembly."

A "water source" is a fluid source from which water can be obtained.

A "zirconium phosphate module" is a sorbent module containing zirconium phosphate.

A "zirconium phosphate module inlet" is a connector through which a fluid, slurry, or aqueous solution can enter a zirconium phosphate module.

A "zirconium phosphate module outlet" is a connector through which a fluid, slurry, or aqueous solution can exit a zirconium phosphate module.

Zirconium Phosphate Recharging

The invention is drawn to systems and methods for recharging and reusing zirconium phosphate in a reusable zirconium phosphate sorbent module. FIG. 1 illustrates a recharger for recharging zirconium phosphate in a zirconium phosphate sorbent module. The recharger includes at least a first receiving compartment 101 for receiving a zirconium phosphate module. The receiving compartment 101 has a zirconium phosphate inlet and a zirconium phosphate outlet (not shown) for connecting to an inlet and outlet of a zirconium phosphate module (not shown). Door 103 controls access to the receiving compartment 101. A user interface 102 can receive information from a user for controlling the recharge process. The recharger can optionally include a second receiving compartment 104 for receiving a second zirconium phosphate module, or a module containing a different sorbent material for concurrent recharging of sorbent materials. The recharger can include any number of receiving compartments for receiving multiple zirconium phosphate modules or various combinations of zirconium phosphate and other sorbent modules. The recharger can have 1, 2, 3, 4, 5, or more receiving compartments for recharging any number of sorbent modules. The recharger can be fluidly connected to one or more recharge solution sources through a recharging flow path. Pumps and valves (not shown) control the movement of fluid from the recharge solution sources through the zirconium phosphate module.

Zirconium phosphate is recharged by pumping one or more solutions containing acids, bases, and sodium salts through the zirconium phosphate module. The hydrogen and sodium ions in the recharge solutions displace potassium, calcium, magnesium, ammonium, and other ions from either the dialysate or source water that are bound and adsorbed by the zirconium phosphate during use. The recharged zirconium phosphate with sodium and hydrogen ions can be used during dialysis to remove cation solutes from the used dialysate.

Figure 2:
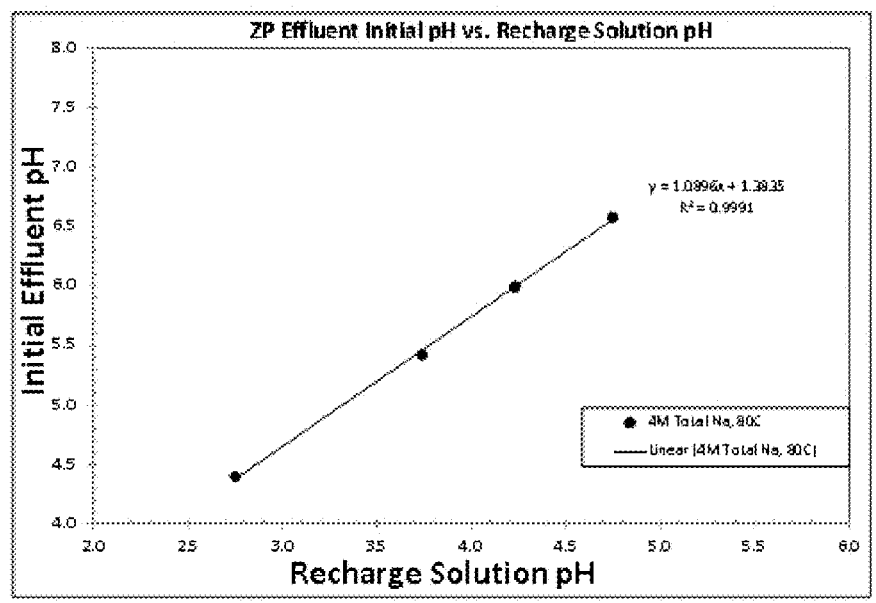
FIG. 2 shows a graph of the initial zirconium phosphate effluent pH as a function of the recharge solution pH.

The initial therapy zirconium phosphate effluent pH depends on the ratio of hydrogen to sodium ions on the zirconium phosphate. FIG. 2 illustrates the effect of the recharge solution pH on the initial therapy zirconium phosphate effluent pH. The recharge solutions in FIG. 2 each contain mixtures of sodium chloride, sodium acetate, and acetic acid. The total sodium concentration in each recharge solution is 4 M, with the ratio of sodium acetate to acetic acid varied to control the pH. As illustrated in FIG. 2, the pH of the recharge solution controls the initial therapy zirconium phosphate effluent pH. One of ordinary skill in the art will understand the initial therapy zirconium phosphate effluent pH can be controlled by adjusting the pH of the recharge solution to result in a desired initial therapy zirconium phosphate effluent pH. The zirconium phosphate effluent pH can be customized based on the needs of the user by controlling the pH of the recharge solution.

Figure 3:
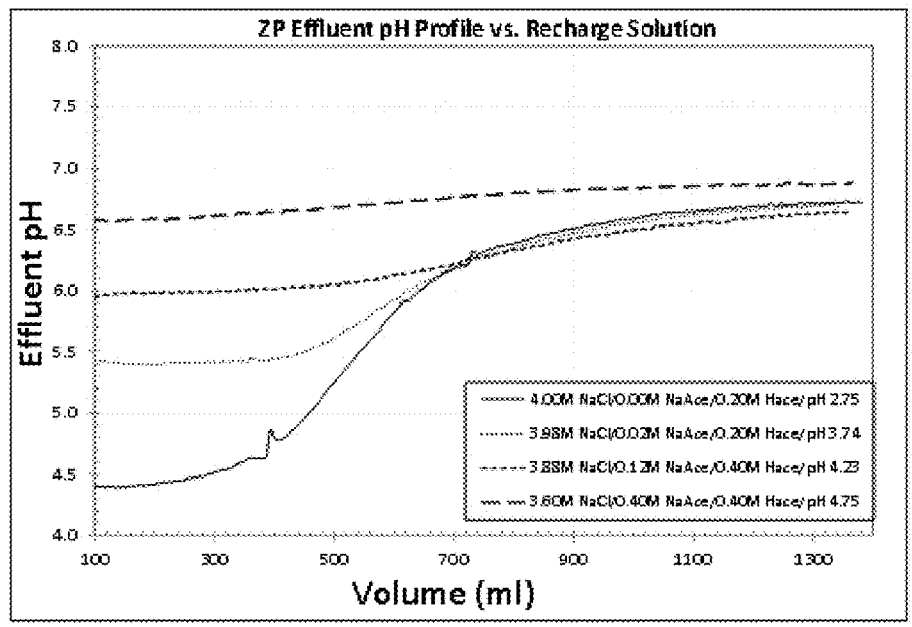
FIG. 3 shows a graph of the zirconium phosphate effluent pH as a function of an amount of fluid passed through the zirconium phosphate module for recharge solutions having various concentrations of acid, base, and salt.

FIG. 3 illustrates the zirconium phosphate effluent pH as a function of the volume of dialysate pumped through the zirconium phosphate module during dialysis. As illustrated in FIG. 3, the initial zirconium phosphate effluent pH is determined by the recharge solutions used. The pH profile of the zirconium phosphate depends on the mass of the zirconium phosphate and the mass of bicarbonate pumped through the zirconium phosphate module. With a high zirconium phosphate mass, and a low bicarbonate mass pumped through the zirconium phosphate, the initial zirconium phosphate effluent pH may be maintained for an entire therapy session. The zirconium phosphate acts like a buffer and as more bicarbonate is pumped through the zirconium phosphate, the buffer capacity becomes exceeded and the pH will start to increase. Without being limited to any theory of invention, the final pH plateau may be related to the composition and pH of the spent dialysate that is pumped through the zirconium phosphate module. However, the initial therapy zirconium phosphate effluent pH is dependent on the pH of the recharge solution.

Table 1 provides non-limiting examples of recharge solutions and the resulting initial therapy zirconium phosphate effluent pH. In each case, the recharge solution was heated to 80° C. prior to use. As shown in Table 1, a higher ratio of sodium acetate to acetic acid results in a higher recharge solution pH, and therefore a higher initial therapy zirconium phosphate effluent pH. The relative amounts of acid, base, and sodium salt can be set to generate a recharge solution having the desired pH.

TABLE 1

| Solution | Total Na (M) | NaCl (M) | NaAce (M) | HAce (M) | pH | Initial Effluent PH |
|---|---|---|---|---|---|---|
| 1 | 4.00 | 4.00 | 0.00 | 0.20 | 2.75 | 4.40 |
| 2 | 4.00 | 3.98 | 0.02 | 0.20 | 3.74 | 5.42 |
| 3 | 4.00 | 3.88 | 0.12 | 0.40 | 4.23 | 5.99 |
| 4 | 4.00 | 3.60 | 0.40 | 0.40 | 4.75 | 6.58 |

Each of the recharge solutions in Table 1 are combinations of sodium chloride, sodium acetate, and acetic acid. One of skill in the art will understand other buffer combinations can be used in place of sodium acetate and acetic acid, including sodium citrate and citric acid, glycolic acid and sodium glycolate, propionic acid and sodium propionate, phosphoric acid and sodium phosphate, or any combination thereof. The relative amounts of sodium chloride and buffer to achieve a desired initial therapy zirconium phosphate effluent pH will depend on the pKa of the acid used, and can be varied as needed.

The zirconium phosphate module effluent pH affects the amount of bicarbonate needed during dialysis. Urease in the sorbent cartridge converts urea to carbon dioxide and ammonium ions. The carbon dioxide produced is in equilibrium with bicarbonate in the dialysate. The carbon dioxide must be removed from the dialysate by a degasser prior to the dialysate entering the dialyzer. The degasser can be any type of degasser known in the art for use in dialysis systems. A high zirconium phosphate effluent pH during therapy drives the equilibrium towards bicarbonate formation, resulting in too much bicarbonate in the dialysate for safe treatment. A low zirconium phosphate effluent pH during therapy drives the equilibrium towards carbon dioxide formation, requiring addition of bicarbonate to the dialysate and placing a high burden on the degasser. One type of degasser suitable for removing carbon dioxide is a membrane contactor. A membrane contractor is a dual chamber device with a hydrophobic microporous membrane separating the chambers. The hydrophobic microporous membrane allows gas transport without allowing water transport across the membrane. Liquid containing gas—in this case $CO_2$—is passed on one side of the membrane and either inert gas or a vacuum is applied to the chamber on the opposite side of the membrane. $CO_2$ is transported from the liquid by diffusion. Another example of a degasser is a vacuum degasser. A vacuum degasser is a chamber in which a vacuum can be applied and which is fluidly connected to a liquid containing gas to be removed. The liquid is sprayed or atomized in the vacuum chamber. The high surface area of the liquid droplets allows efficient removal of the gas. One of skill in the art will understand that any device capable of removing $CO_2$ from the dialysate can be used. The zirconium phosphate effluent pH can be controlled by the pH of the recharge solution to meet the needs of the patient and system. The zirconium phosphate effluent pH is a function of the pH, pKa, buffer capacity, sodium chloride level, and temperature of the recharge solution. As described, a control system can automatically determine the volumes of each component needed to achieve a desired initial therapy zirconium phosphate effluent pH based on each of the factors.

A zirconium phosphate effluent pH of about 6.5 allows greater than 5% of patients to be treated with a dialysate bicarbonate concentration of 25 mM. At a higher pH, fewer patients can be treated. For example, only about 40% of patients can be treated with a zirconium phosphate effluent pH of 6.9 and a dialysate bicarbonate level of 25 mM. At a very low pH, too much acid is created and additional bicarbonate will not be enough to keep the dialysate pH within a safe range, and a degasser is needed to remove carbon dioxide. The initial therapy zirconium phosphate effluent pH can be set at any value capable of generating safe dialysate, including between 4.0 and 6.9. A dialysate with a lower pH places a higher burden on the degasser.

Any combination of acid, base, and sodium salt capable of generating a recharge solution within the desired pH range can be used in recharging the zirconium phosphate. Non-limiting examples of acids and bases include sodium acetate and acetic acid, sodium citrate and citric acid, glycolic acid and sodium glycolate, propionic acid and sodium propionate, phosphoric acid and sodium phosphate, or any combination thereof. One of skill in the art will understand the relative amounts of acid and base needed to generate a recharge solution with a desired pH will vary with the pKa of the acid. The relative volumes of the acid and base can be varied based on the pKa of the particular acid and base used. For example, a recharge solution with 3.1 M sodium chloride, 0.9 M sodium acetate, and 0.6 M acetic acid has a pH of 4.6, which will generate a zirconium phosphate effluent pH of 6.5.

As described, the zirconium phosphate effluent pH during therapy controls the equilibrium between carbon dioxide and bicarbonate in the dialysate. Carbon dioxide and bicarbonate in the dialysate generally comes from two sources, the conversion of urea to carbon dioxide and any bicarbonate added to the dialysate. To minimize the amount of additional bicarbonate required, the zirconium phosphate effluent pH can be set to a higher value, at least for patients that can be effectively treated with a higher dialysate bicarbonate level. The higher zirconium phosphate effluent pH during therapy drives the bicarbonate/carbon dioxide equilibrium towards bicarbonate formation, retaining bicarbonate generated from the urea removed from the patient.

A control system in the recharger can determine the optimal initial therapy zirconium phosphate effluent pH for a patient based on the patient's pre-treatment bicarbonate and urea levels. For alkalotic patients, a lower initial therapy zirconium phosphate effluent pH can be selected to minimize the amount of bicarbonate formed from the patient's urea. For other patients, a higher initial therapy zirconium phosphate effluent pH can be selected to generate a higher amount of bicarbonate from the patient's urea, reducing the additional bicarbonate needed and minimizing the burden on the degasser. Alternatively, a user interface can be provided, with the user directly inputting the desired initial therapy zirconium phosphate effluent pH.

The control system can be any component capable of monitoring and affecting the states of the recharger. The control system can use processors, memory and computer components to carry out the functions described. The control system is in communication with the pumps and valves of the recharging flow paths and can control the pumps and valves in accordance with stored instructions. The control system is also in communication with various sensors in the recharging flow paths. The control system receives data from the sensors and controls the pumps and valves of the recharging flow path on the basis of the data in accordance with stored instructions. Factors affecting the desired initial therapy zirconium phosphate effluent pH, such as patient pre-treatment urea and bicarbonate levels can be communicated to the control system by any means known in the art. The control system can automatically determine the optimal recharging solution pH using mathematical algorithms or look-up tables, and operate the pumps and valves of the recharging flow paths to control the recharging process.

Figure 4:
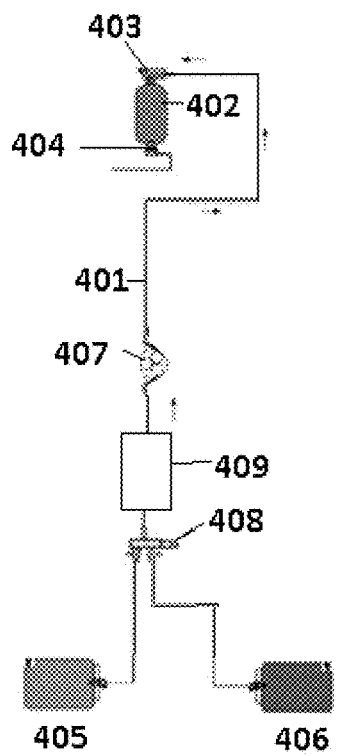
FIG. 4 is a recharging flow path for recharging a zirconium phosphate module with two recharge solution sources.

FIG. 4 illustrates a non-limiting embodiment of a recharging flow path for customization of a recharging solution. A zirconium phosphate module 402 can connect to the recharging flow path 401 through zirconium phosphate inlet 403 and zirconium phosphate outlet 404. Pump 407 provides a driving force for moving fluids through the recharging flow path 401. A salt or brine source 405, containing a salt solution such as sodium chloride or mixtures of sodium chloride and sodium acetate, and an acid source 406 containing an acid solution, such as acetic acid, are fluidly connected to the recharging flow path 401. Valve 408 determines the amount of each recharge solution that enters the recharging flow path 401 to generate a recharge solution having a specified acid concentration, base concentration, and salt concentration, and can be controlled by the control system. Sodium chloride and/or sodium acetate from brine source 405 is pumped through the recharging flow path 401 to the zirconium phosphate module 402. Acid from acid source 406 can be pumped into the recharging flow path 401 at a ratio to the sodium chloride and sodium acetate based on the desired recharge solution pH. For example, acetic acid from acid source 406 can be metered in to the sodium chloride and/or sodium acetate in recharging flow path 401 at a specified rate to control the pH of the resulting recharge solution. A higher sodium chloride to acid ratio will result in a recharge solution at a higher pH, while a lower sodium chloride to acid ratio will result in a recharge solution at a lower pH. The control system can automatically control valve 408 to control the ratio of sodium chloride to acid. Alternatively, the acid source 406 can contain a buffer solution, such as sodium acetate and acetic acid, and the control system can control the ratio of sodium chloride and buffer to control the recharge solution pH. A static mixer 409 can be included to ensure complete mixing of the acid and sodium solutions. Alternatively, the acid and sodium solutions can be mixed through the mixing of the two fluid streams in the recharging flow path 401. One of skill in the art will understand that different pump and valve arrangements can be used with the system illustrated in FIG. 4. For example, the brine source 405 and acid source 406 can be connected to the recharging flow path 401 through separate pumps, allowing simultaneous addition of sodium chloride and acid to the recharging flow path 401.

Alternatively, a system as illustrated in FIG. 4 can have sodium chloride and an acid in a first recharge solution source, with a base solution, such as sodium hydroxide, in a base source. The sodium chloride and acid can be pumped through the zirconium phosphate module, with the base solution metered in to generate a recharge solution with the desired pH in situ.

The recharging flow path 401 in FIG. 4 can also recharge the zirconium phosphate module 402 by addition of recharging solutions in a sequential order. The acid solution from acid source 406 can be pumped through the zirconium phosphate module 402 first, followed by sodium chloride and sodium acetate from brine source 405. The initial acid solution will generate a zirconium phosphate module 402 at a low pH, and the later addition of sodium chloride and sodium acetate will raise the pH as sodium ions displace the hydrogen ions initially adsorbed by the zirconium phosphate. The resulting zirconium phosphate effluent pH will depend on the amount of sodium chloride and sodium acetate pumped through the zirconium phosphate module 402 in the second step. The control system can control the sodium chloride and sodium acetate addition to generate a zirconium phosphate module 402 with the desired initial therapy zirconium phosphate effluent pH. A pH sensor (not shown) can be placed in the zirconium phosphate effluent to determine the zirconium phosphate effluent pH, and the sodium chloride can be stopped when the pH sensor reads the desired pH. The concentration and amount of sodium chloride and sodium acetate pumped through the zirconium phosphate module 402 will control the initial therapy zirconium phosphate effluent pH after recharging. Alternatively, the sodium chloride and sodium acetate can be pumped through the zirconium phosphate module 402 first, followed by the acid.

Figure 5:
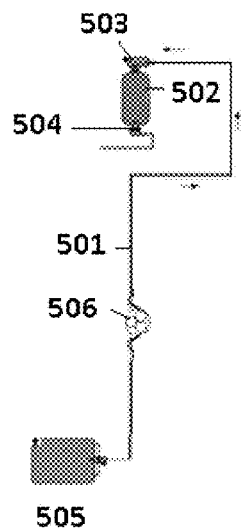
FIG. 5 is a recharging flow path for recharging a zirconium phosphate module with a single recharge solution source.

FIG. 5 illustrates a recharging flow path 501 with a single recharge solution source 505 containing a sodium salt and buffer. A zirconium phosphate module 502 can connect to the recharging flow path 501 through zirconium phosphate inlet 503 and zirconium phosphate outlet 504. Pump 506 provides a driving force for moving fluids through the recharging flow path 501. Recharge solution source 505 is fluidly connected to the recharging flow path 501. A recharge solution in recharge solution source 505 at the desired recharge solution pH can be pumped through the zirconium phosphate module 502 to recharge the zirconium phosphate. To alter the initial therapy zirconium phosphate effluent pH, the pH of the recharge solution can be altered. The user can add solid or concentrated sources of an acid, a base, a salt, or combinations thereof, to control the pH of the recharge solution to generate a recharge solution having a specified acid concentration, base concentration, and salt concentration. The control system can inform the user of the correct amounts of acid, base, or salt to add to the recharge solution source 505. Alternatively, a separate source of acid, base, or salt can be included in the recharger, and the system can automatically add the correct amount to the recharge solution source 505 based to generate a recharge solution with the desired pH. For example, a recharge solution with a pH of 4.6 can be placed in the recharge solution source 505 and used for the majority of patients. For severely alkalotic patients, the system or user can add a predetermined amount of acid to lower the recharge solution pH. To reduce the amount of bicarbonate needed during therapy, the system or user can add a predetermined amount of base to raise the recharge solution pH.

One of skill in the art will understand the recharging flow paths illustrated in FIGS. 4-5 can include additional fluid sources. A water source can provide water for flushing and rinsing of the zirconium phosphate module before and after recharging. A water source can also provide in-line dilution of any of the recharge solutions, allowing a more concentrated recharge solution in the recharge solution sources. A disinfectant source can provide a disinfection solution for disinfecting the zirconium phosphate module prior to recharging. The disinfection solution can be any solution capable of disinfecting the zirconium phosphate module, including a peracetic acid solution, a citric acid solution, or any other disinfectant.

The total volume of recharge solution needed to recharge the zirconium phosphate depends on the amount of cations removed by the zirconium phosphate in the previous dialysis session, and in particular the pre-dialysis patient potassium, calcium, magnesium, and urea levels. Other factors include patient weight, bicarbonate level, dialysate flow rate, blood flow rate, dialyzer size, dialysis time, ultrafiltration rate, the size of the zirconium phosphate sorbent module, and the potassium, calcium, magnesium, and bicarbonate dialysis prescription. Usage of a zirconium phosphate module by a patient can be tracked with an RFID tag, barcode, or other tracking device. The control system can receive any one or more of the patient parameters influencing the amount of recharge solution needed, and determine the necessary volume of the recharge solution for recharging the zirconium phosphate module.

A tracking component, such as an RFID tag or bar code, can be affixed to the zirconium phosphate module, and automatically read by the control system at various times, including prior to dialysis, after dialysis, prior to recharging, and after recharging. A single reader can read and track the zirconium phosphate module at each stage of use, or separate readers can be included with the rechargers and dialysis systems to track usage of the zirconium phosphate module. The tracking system can track which patients used the zirconium phosphate module and the dialysis parameters that affect the amount of cations removed by the zirconium phosphate module. The parameters can be communicated to the control system, which can then determine the amount of recharge solution necessary through mathematical algorithms, look-up tables or a combination thereof. Generally, between 6 and 7 total moles of sodium are needed per mole of cations loaded on the zirconium phosphate for full recharging at elevated temperatures, and less recharge solution is needed with a higher recharge solution concentration. A higher amount of sodium may be needed if the recharging is conducted at room temperature. The recharge solution can have any amount of sodium ions relative to the amount of cations loaded on the zirconium phosphate, including sodium ions between 5 and 15 times greater than the amount of cations loaded on the zirconium phosphate. The amount of recharge solution needed can also depend on the temperature of the recharge solution. The recharging flow paths described can include a heater and optionally a heat exchanger for heating the recharge solution to a specified temperature prior to pumping the recharge solution through the zirconium phosphate module, as recharging zirconium phosphate may be more efficient at elevated temperatures. A temperature sensor determines the temperature of the recharge solution, and the control system can take temperature into account in determining the total amount of recharge solution necessary. The recharge solution can be heated to any specified temperature, including between 60-90° C., 60-70° C., 60-80° C., 75-85° C., or 80-90° C. During recharging, the control system can use only the volume of recharge solution necessary based on the total amount of cations loaded onto the zirconium phosphate, the concentration of the recharge solution, and the temperature of the recharge solution, saving on costs and materials.

Figure 6:
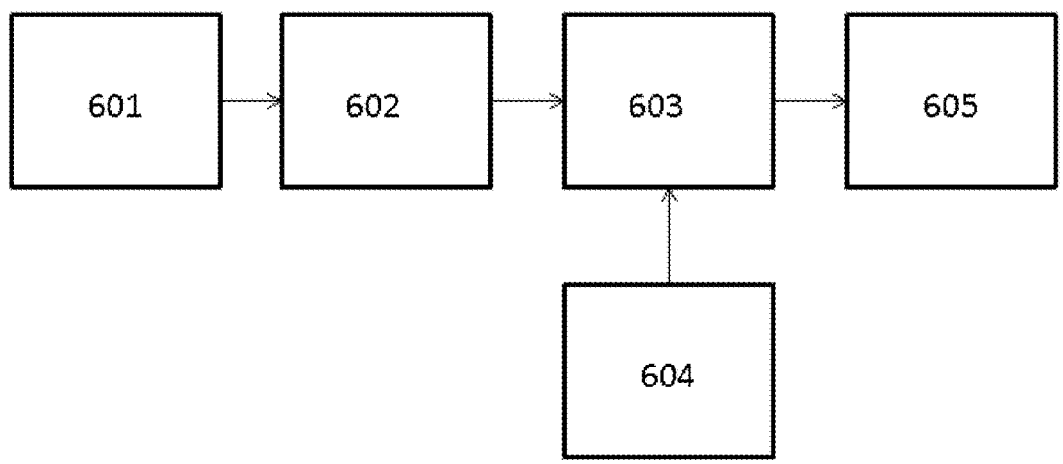
FIG. 6 is a flow chart illustrating the steps in customizing a zirconium phosphate recharging process.

FIG. 6 is a flow chart illustrating the steps in customizing a zirconium phosphate recharging process based. In step 601, a desired initial therapy zirconium phosphate effluent pH can be determined. As described, the desired initial therapy zirconium phosphate effluent pH can be based on one or more patient parameters and system parameters, including the patient's pre-treatment bicarbonate and urea levels, as well as the available of additional bicarbonate to be added during dialysis and the degassing capabilities of the system. The desired initial therapy zirconium phosphate effluent pH can be determined by the control system based on the patient parameters and/or system parameters, or directly entered by a user through a user interface. In step 602 the concentrations of acid, base, and sodium salt in the recharge solution can be determined. The described concentrations depend on the pKa of the acid or buffer, the buffer capacity, and the temperature of the recharge solution, and can be automatically determined by the control system. Where a single recharge solution source is used, the control system can automatically inform the user to add a specific amount of acid, base, or salt to the recharge solution. Where two or more recharge solution sources are used, the control system can determine the relative amounts of fluid needed from each recharge solution source.

In step 604, the system can determine an amount of cations removed by the zirconium phosphate module in a previous dialysis session. The amount of cations removed by the zirconium phosphate module depends on the pre-dialysis patient potassium, calcium, magnesium, and urea levels of the patient, as well as patient weight, patient bicarbonate level, dialysate flow rate, blood flow rate, dialyzer size, dialysis time, ultrafiltration rate, and the potassium, calcium, magnesium, and bicarbonate dialysis prescription. The described patient parameters can automatically be received by the control system through a tracking device on the zirconium phosphate module tracking usage. Alternatively, the described patient parameters can be input directly by the user based on the patient's medical records or other information. The described patient parameters can also be assumed by the system based on patient norms and settings entered into the system based on patient blood labs.

In step 603, the amount of acid, base, and sodium salt necessary to achieve the desired initial therapy zirconium phosphate effluent pH can be determined. Using the total volume determined in step 604, and the concentrations determined in step 602, the control system can automatically determine the pump rates and/or valve switching necessary to recharge the zirconium phosphate from one or more recharge solution sources and control the pumps and valves to generate the recharge solution. In step 605, the control system controls the pumps and valves to recharge the zirconium phosphate module.

One of skill in the art will understand that one or more of the steps illustrated in FIG. 6 can be eliminated. For example, if a desired initial therapy zirconium phosphate effluent pH of 6.5 will be used for nearly all patients, the system can skip steps 601 and 602. The concentrations of the acid, base, and salt necessary to generate a recharge solution with the correct pH can be stored in a system memory and used each time. If a specified recharge solution volume is used each time, step 604 can also be eliminated.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination, or follow a preferred arrangement of one or more of the described elements.

We claim:

1. A method, comprising the steps of:
   determining a desired initial therapy zirconium phosphate effluent pH based on one or more patient parameters; and
   recharging zirconium phosphate in a zirconium phosphate module by pumping one or more recharge solutions through the zirconium phosphate module; the one or more recharge solutions comprising an acid solution, a base solution, a buffer solution, a salt solution, water, or combinations thereof;
   wherein the one or more recharge solutions have an acid concentration, a base concentration, a buffer concentration, and a salt concentration to result in the desired initial therapy zirconium phosphate effluent pH.

2. The method of claim 1, wherein the step of pumping the one or more recharge solutions through the zirconium phosphate module comprises pumping multiple recharge solutions through the zirconium phosphate module in a sequential order.

3. The method of claim 2, wherein the sequential order comprises a first recharge solution containing an acid or buffer, and a second recharge solution containing a sodium salt; or a first recharge solution containing a sodium salt and a second recharge solution containing an acid or buffer.

4. The method of claim 3, wherein the buffer contains acetic acid and sodium acetate.

5. The method of claim 1, wherein the desired initial therapy zirconium phosphate effluent pH is between 4.0 and 6.9.

6. The method of claim 1, wherein a single recharge solution is pumped through the zirconium phosphate module.

7. The method of claim 6, wherein the single recharge solution is a solution of acetic acid, sodium acetate, and sodium chloride.

8. The method of claim 6, wherein the single recharge solution has a pH of between 4.2 and 5.0.

9. The method of claim 1, further comprising the step of determining an amount of cations removed by the zirconium phosphate module in a dialysis session prior to the step of pumping one or more recharge solutions through the zirconium phosphate module.

10. The method of claim 9, wherein a volume of recharge solution used is based, at least in part, on the amount of cations removed by the zirconium phosphate module.

11. The method of claim 9, wherein the one or more recharge solutions contains sodium ions in an amount of between 5 and 15 times greater than the amount of cations removed by the zirconium phosphate module.

12. The method of claim 1, further comprising the step of heating the one or more recharge solutions to a specified temperature prior to pumping the one or more recharge solutions through the zirconium phosphate module.

13. The method of claim 12, wherein the acid concentration, the base concentration, the buffer concentration, and the salt concentration are set based at least in part on the specified temperature.

14. A recharger comprising:
   a receiving compartment comprising a zirconium phosphate module inlet and a zirconium phosphate module outlet;
   one or more recharge solution sources, wherein the one or more recharge solution sources are selected from the group consisting of an acid source, a base source, a salt source, a water source, and combinations thereof;
   a recharging flow path fluidly connected to the one or more recharge solution sources and the zirconium phosphate module inlet, and comprising at least one pump;
   a control system determining a desired initial therapy zirconium phosphate effluent pH, and determining a concentration of an acid, a base, a buffer, a salt, or combinations thereof to result in the desired initial therapy zirconium phosphate effluent pH; and
   the control system controlling an amount of each recharge solution pumped through the recharging flow path.

15. The recharger of claim 14, further comprising one or more valves fluidly connected to the one or more recharge solution sources and the recharging flow path.

16. The recharger of claim 14, further comprising a heater and temperature sensor in the recharging flow path.

17. The recharger of claim 15, the control system determining a volume of acid, base, buffer, and salt for recharging a zirconium phosphate module based at least in part on a temperature of one or more recharge solutions.

18. The recharger of claim 14, the control system determining a volume of the acid, the base, the buffer, and the salt for recharging a zirconium phosphate module based at least in part on an amount of cations removed by the zirconium phosphate module during a dialysis session.

19. The recharger of claim 14, wherein the one or more recharge solution sources comprise at least two recharge solution sources.

20. The recharger of claim 18, further comprising a static mixer in the recharging flow path for mixing of the acid, base, buffer, or salt.

* * * * *